(12) United States Patent
Wolf et al.

(10) Patent No.: US 10,585,210 B2
(45) Date of Patent: Mar. 10, 2020

(54) APPARATUS FOR RADIOMETRIC CORRECTION AND ORTHORECTIFICATION OF AERIAL IMAGERY

(71) Applicant: Arable Labs, Incorporated, Princeton, NJ (US)

(72) Inventors: Adam Wolf, Princeton, NJ (US); Brenden Duffy, Rockville Centre, NY (US); Lyndon Estes, Princeton, NJ (US)

(73) Assignee: Arable Labs, Inc., Princeton, NJ (US)

(*) Notice: Subject to any disclaimer, the term of this patent is extended or adjusted under 35 U.S.C. 154(b) by 466 days.

(21) Appl. No.: 15/287,505

(22) Filed: Oct. 6, 2016

(65) Prior Publication Data

US 2018/0180768 A1 Jun. 28, 2018

Related U.S. Application Data

(60) Provisional application No. 62/237,679, filed on Oct. 6, 2015.

(51) Int. Cl.
*G06T 7/00* (2017.01)
*G01W 1/02* (2006.01)
(Continued)

(52) U.S. Cl.
CPC .............. *G01W 1/02* (2013.01); *G01J 3/00* (2013.01); *G01W 1/08* (2013.01); *G01W 1/12* (2013.01); *G01W 1/14* (2013.01); *G06T 7/70* (2017.01); *G01N 33/0098* (2013.01); *G01N 33/246* (2013.01); *G01N 2033/245* (2013.01);
(Continued)

(58) Field of Classification Search
CPC B64C 2201/123; G01C 11/02; G06K 9/0063; G01J 3/2823; G06T 2207/0032; G06T 3/4038; G06T 7/80
See application file for complete search history.

(56) References Cited

U.S. PATENT DOCUMENTS

| | | |
|---|---|---|
| 3,390,576 A | 7/1968 | Yellott |
| 3,708,667 A | 1/1973 | Denis et al. |

(Continued)

FOREIGN PATENT DOCUMENTS

| | | |
|---|---|---|
| CN | 201298082 Y | 8/2009 |
| EP | 2835622 A1 | 2/2015 |

(Continued)

OTHER PUBLICATIONS

Microarial Projects LLC, "Mapping without ground control points, does it work?", sUAS News 2015.
(Continued)

*Primary Examiner* — Mohamed Charioui
*Assistant Examiner* — Christine Y Liao
(74) *Attorney, Agent, or Firm* — Ulmer & Berne LLP

(57) ABSTRACT

The present inventors have developed a ground station that, when installed in a field, can collect upwelling and downwelling radiation, and GPS location coordinates, Data from remotely sensed imagery (RSI) can be used to monitor crop health. Use of the ground station can obviate the need for personnel to be deployed into the field during drone overflights for management of agriculture.

25 Claims, 10 Drawing Sheets
(9 of 10 Drawing Sheet(s) Filed in Color)

(51) Int. Cl.

| | |
|---|---|
| *G01W 1/12* | (2006.01) |
| *G01W 1/08* | (2006.01) |
| *G01W 1/14* | (2006.01) |
| *G06T 7/70* | (2017.01) |
| *G01J 3/00* | (2006.01) |
| *G01N 33/24* | (2006.01) |
| *G01N 33/00* | (2006.01) |

(52) U.S. Cl.
CPC ............... *G06T 2207/10036* (2013.01); *G06T 2207/30188* (2013.01)

(56) References Cited

U.S. PATENT DOCUMENTS

| | | |
|---|---|---|
| 3,876,880 A | 4/1975 | Guicherd |
| 4,264,211 A | 4/1981 | Biggs |
| 4,373,809 A | 2/1983 | Gobrecht |
| 4,491,727 A | 1/1985 | Appelbaum et al. |
| 4,796,284 A | 1/1989 | Jenkins |
| 4,850,713 A | 7/1989 | Thery et al. |
| 5,331,168 A | 7/1994 | Beaubien et al. |
| 6,160,902 A | 12/2000 | Dickson et al. |
| 6,297,740 B1 | 10/2001 | Hill et al. |
| 6,393,927 B1 | 5/2002 | Biggs et al. |
| 6,396,040 B1 | 5/2002 | Hill |
| 6,417,500 B1 | 7/2002 | Wood |
| 7,157,678 B2 | 1/2007 | Maldziunas et al. |
| 7,362,439 B2 | 4/2008 | Franzen et al. |
| D686,929 S | 7/2013 | Rainer et al. |
| 8,891,895 B2 | 11/2014 | Garrett et al. |
| 9,002,660 B2 | 4/2015 | Mannstein et al. |
| 9,037,521 B1 | 5/2015 | Mewes et al. |
| 9,104,201 B1* | 8/2015 | Pillai ............... B64C 39/024 |
| 9,131,644 B2 | 9/2015 | Osborne |
| 9,201,991 B1 | 12/2015 | Mewes et al. |
| D747,984 S | 1/2016 | Zhao et al. |
| 9,268,061 B2 | 2/2016 | Salmi |
| 9,292,796 B1 | 3/2016 | Mewes et al. |
| 9,342,899 B2 | 5/2016 | Gao et al. |
| 9,442,496 B1* | 9/2016 | Beckman ............ G10K 11/178 |
| 9,488,630 B2 | 11/2016 | Coram et al. |
| D799,998 S | 10/2017 | Wolf et al. |
| 9,841,533 B2 | 12/2017 | Wolf et al. |
| 9,939,319 B2 | 4/2018 | Wolf et al. |
| 10,156,475 B2 | 12/2018 | Wolf et al. |
| 2006/0043297 A1 | 3/2006 | Ouvrier-Buffet et al. |
| 2007/0097371 A1 | 5/2007 | Parker |
| 2007/0215794 A1 | 9/2007 | Cernasov et al. |
| 2007/0281129 A1 | 12/2007 | Chan et al. |
| 2007/0285654 A1 | 12/2007 | Hardcastle |
| 2008/0002185 A1 | 1/2008 | Gitelson et al. |
| 2008/0259318 A1 | 10/2008 | Pan et al. |
| 2010/0066537 A1* | 3/2010 | Weller ............... G08B 25/009 340/565 |
| 2010/0115830 A1 | 5/2010 | Dubé |
| 2011/0273704 A1 | 11/2011 | Burba |
| 2012/0112072 A1 | 5/2012 | Jones et al. |
| 2012/0173147 A1 | 7/2012 | Mannstein et al. |
| 2012/0235041 A1 | 9/2012 | Reda |
| 2012/0275651 A1* | 11/2012 | Brown ............... G06K 9/0063 382/103 |
| 2013/0014556 A1 | 1/2013 | Salmi |
| 2013/0104646 A1 | 5/2013 | Dolce |
| 2013/0176423 A1* | 7/2013 | Rischmuller ....... G05D 1/0038 348/114 |
| 2014/0016121 A1 | 1/2014 | MacDonald |
| 2014/0168734 A1 | 6/2014 | Dell'Eva et al. |
| 2015/0015697 A1 | 1/2015 | Redden et al. |
| 2015/0355017 A1 | 12/2015 | Clarke et al. |
| 2016/0041035 A1 | 2/2016 | Allen et al. |
| 2016/0063420 A1 | 3/2016 | Tomii et al. |
| 2016/0069741 A1* | 3/2016 | Ritter ............... G01J 3/0297 356/402 |
| 2016/0084635 A1 | 3/2016 | Pittman et al. |
| 2016/0231171 A1 | 8/2016 | Assefa et al. |
| 2017/0223947 A1 | 8/2017 | Gall et al. |
| 2017/0261647 A1 | 9/2017 | Wolf et al. |
| 2018/0010963 A1 | 1/2018 | Wolf et al. |
| 2018/0188109 A1 | 7/2018 | Wolf et al. |

FOREIGN PATENT DOCUMENTS

| | | |
|---|---|---|
| JP | 02298828 A | 12/1990 |
| WO | 2013060637 A1 | 5/2013 |
| WO | 2013181408 A2 | 12/2013 |
| WO | 2014091314 A2 | 6/2014 |
| WO | 2016140566 A1 | 9/2016 |
| WO | 2018009574 A1 | 1/2018 |

OTHER PUBLICATIONS

Thomas, C. S., Gubler, W. D., and Leavitt, G., Field testing of a powdery mildew disease forecast model on grapes in California, Phytopathology, 1994, 84,1070.

Bao, Y. et al., Estimation of winter wheat biomass based on remote sensing data at various spatial and spectral resolutions, Front Earth Sci. China 2009, 3(1), 118-128.

Jin, Y., et al., Remote Sensing-Based Biomass Estimation and Its Spatio-Temporal Variations in Temperate Grassland, Northern China, Remote Sens., 2014, 6, 1496-1513.

Wang, J., et al., Relations between NDVI, Grassland Production, and Crop Yield in the Central Great Plains., Geocarto International, Sep. 2005, 20(3), 5-11.

Gubler, W. D., et al., Use of a weather station based disease risk assessment for control of grapevine powdery mildew in California, Phytopathology 1997, 87, S36.

Asano et al., "A Multichannel Cloud Pyranometer System for Airborne Measurement of Solar Spectral Reflectance by Clouds", Journal of Atmospheric and Oceanic Technology, Jun. 1995, pp. 479-487.

Shambel Maru Moges, "Differences Between Red and Green NDVI, What they Predict and What they Do Not Predict", Student Presentation, Oklahoma State University, SOIL/BAE 4213 Precision Agriculture, May 2, 2001, 18 pages.

Myers, "Quantitative Analysis of Spectral Impacts on Silicon Photodiode Radiometers", Solar 2011 NREL Conference Paper, Apr. 2011, 8 pages.

Agisoft LLC, "Tutorial (Beginner level): Orthophoto and DEM Generation with Agisoft PhotoScan Pro 1.1 (without Ground Control Points)", 2015, 11 pages.

Microarial Projects LLC, "Mapping without Ground Control Points: Does it Work?", White Paper, Sep. 2015, 6 pages.

Decagon Devices, Inc., "SRS Spectral Reflectance Sensors: Operator's Manual", Jul. 2017, 38 pages.

International Search Report and Written Opinion received for International Application No. PCT/US2017/040759, dated Sep. 11, 2017, 25 pages.

Arain, M.A., et al.: "Year-round observations of the energy and water vapour fluxes above a boreal black spruce forest." Hydrological Processes 17.18 (2003): 3581-3600.

\* cited by examiner

Image coordinates of Ground-Based Devices
(X, Y)

Affine Transformation:
- Translate
- Rotate
- Scale

True Coordinates of Ground-Based Devices
(Latitude, Longitude)

Stage 1: Bud  Stage 2: Flower

Stage 3: Sm Green  Stage 4: Lg Green

Stage 5: White  Stage 6: Pink

APPARATUS FOR RADIOMETRIC CORRECTION AND ORTHORECTIFICATION OF AERIAL IMAGERY

CROSS REFERENCE TO RELATED APPLICATION

This application claims benefit of and priority to Provisional Application 62/237,679 filed on Oct. 6, 2015. This application is hereby incorporated by reference in its entirety.

INTRODUCTION

Monitoring of the health of a crop is an important component in the scientific management of agriculture. While measurements of ambient weather conditions are strong correlates to yield, measurements of the plants themselves are potentially more diagnostic for problems, and predictive of eventual yield. Often, the health of plants in a field is measured using imagery in particular diagnostic wavelengths collected by satellite, airplane, and unmanned aerial vehicles (UAVs). One issue with remotely sensed imagery (RSI) as it is conventionally measured, is that observations are not calibrated into reflectances, wherein reflectance is the ratio of upwelling to downwelling radiation within a defined spectral hand. In the absence of such calibration, there is limited ability to account for the illumination conditions at the time and place of measurement. These illumination conditions have a direct bearing on the interpretation of the radiance value, which loses the capacity to be compared with radiance values at other sites or other times with different illumination conditions. A second issue with RSI is the need to transform images to real-world coordinates. The process of geometric correction is essential to enable individual images to be related to other imagery and geospatial data such as parcel maps, roads, landmarks, and other geodatabases.

Aerial imagery collected by airplanes or UAVs (drones) faces at least two problems. First, images must be placed into real-world coordinates; typically a stationary marker (e.g. a feature clearly visible from overhead, such as a road intersection is used as a geo-located position standard for a UPS. Second, to be comparable over time, raw radiance measurements need radiometric correction for conversion into reflectances. These two corrections allow for individual features in the imagery to be compared quantitatively over time.

RSI makes use of so-called "vegetation indices", which are based on arithmetic combinations of individual components of the color spectrum, in particular, two vegetation indices have come into wider use, namely the normalized difference vegetation index (NDVI), which makes use of light measured within the red (650-700) and near-infrared (NIR; 800-900 nm) parts of the electromagnetic spectrum, as well as the "green-NDV", which makes use of the green (495-570 nm) and near infrared parts of the spectrum. NDVI is calculated using the equation; NDVI=(NIR−RED)/(NIR+RED) where NIR is the near-infrared and RED is the reading of visible red light. More recently, imagery collected by drones uses "blue-NDVI", which filter the RED band of a conventional camera into an NIR band, and use BLUE light (400-460 nm) as a measure of visible light, i.e. BNDVI= (NIR−BLUE)/(NIR+BLUE). NDVI imagery has become widespread accompanying the emergence of filter kits that modify consumer cameras to (1) expose the NIR part of the spectrum (which CMOS and CCD cameras are sensitive to, but which are normally blocked), and (2) block the blue or green part of the visible spectrum. Best practices dictate that imagery collected by such cameras be accompanied by images of a surface with a known reflectance spectrum for correcting the imagery post-hoc.

Additionally, RSI is often made using only upwelling radiance incident on a downward-pointed camera, without measuring downwelling radiance originating from the sun, and sky. When measured in this way, the radiances of each pixel cannot be converted into reflectances. This introduces a discrepancy between the theoretical basis of the vegetation index—which is computed based on reflectance—and the actual measurements, which are computed using only upwelling radiance. In the absence of a normalization of radiance into reflectance using the downwelling radiation, there is considerable dependence of the imagery on the illumination conditions at the time of observation, while the objective is typically to measure the properties of the surface independent of the illumination conditions. Thus, in the absence of a measurement of the illumination conditions at the time and place of measurement, there are no means to normalize upwelling radiance into a reflectance product. This compromises the interpretation of the digital value, because it loses the capacity to be compared with other sites or other times with different illumination conditions.

There are methods of computing reflectances from separate downwelling radiation measurements, but all of these measurements rely on extremely precise location information. While the topology of a mosaicked RSI is generally internally consistent—that is, individual images taken in the course of a flight are arranged relative to one another in space—this image mosaic cannot he compared with other imagery collected in different points in time or space without being first transformed into real world coordinates because all of the positional imagery is relative to other positions within the image. The process of assigning real world coordinates to these images is called orthorectification. Orthorectification includes processes such as affine transformations to scale, rotate, and translate the imagery using ground-based control points with known real-world coordinates. Orthorectification can also refer to a process of removing distortion due to elevational differences.

In order to acquire these ground-based control points "around-truthing" or taking ground based measurements by physically going to the field, is required. Therefore, increased use of aircraft and other automatic devices has increased the need for ground-truthing and radiometric correction on a field-by-field basis. Without these in-person measurements, comparisons between RSI data taken at different times is not possible using current methods, although such comparisons are necessary for qualitative and, quantitative assessments of the state of vegetation in a location. Only with these assessments are the data useful for determining the appropriate actions to best support crop growth.

In their white paper, "Mapping without ground control points, does it work?" (sUAS News 2015), Microarial Projects LLC describe the use of parking lot markers such as lines to establish GPS coordinates of fixed points in real space to provide coordinates without performing "ground truthing" for each pass. However, this method does not describe the use of light sensors to collect radiance readings for processing into reflectances.

Reflectance correction and orthorectification currently requires specialized equipment. Typically, reflectance correction employs a surface with a known reflectance spectrum, such as SPECTRALON® (Labsphere, Inc., North Sutton, N.H.) fluoropolymer, which is imaged with the same camera as is employed during aerial survey, to provide calibration to a common standard. This adds operational complexity to routine aerial survey, as the surveyor needs to provide such a target, and then most deploy this target at the time and place of survey. Similarly, orthorectification by current methods requires a site visit by someone with a specialized high-accuracy GPS before the imagery can be processed. Because of the need for centimeter-scale accuracy in the GPS coordinates, expensive GPS equipment is required. These requirements impede the routine correction of RSI. In addition, one issue with commonly used thermal cameras is the lack of calibration to a common thermal standard.

Alternative methods and systems for collecting data required for scientific management of agriculture are therefore needed for improving crop yields.

SUMMARY

The present inventors have developed a ground-based station that can be used for both orthorectification and radiometric correction of imagery collected by piloted or non-piloted craft. The present inventors have developed a device that combines radiometric readings with light sensors in particular spectral bands, and with GPS readings that can be used for post-flight image processing. In various configurations, a series of images or a "movie" can be generated without flickering in terms of the brightness. In various configurations, a station of the present teachings allows imagery to be corrected in a remote and automated fashion by retrospectively retrieving radiometric and positional data collected by die station at the time of vehicle overpass, without a need for personnel in the field to collect such measurements at the time of image collection. In addition, because the station can be deployed for extended periods of time, high accuracy GPS coordinates (e.g., to within about 10 cm or less, or 10 cm or less) can be attained by averaging a time series of individually low accuracy GPS coordinates. This can allow GPS equipment to be used that can be considerably less expensive compared to currently used high-accuracy GPS. Furthermore, data gathered with the aid of the device can be used to assess crop field conditions. A farmer or crop adviser can use the data to assess crop health and crop growth, and make management decisions such as, for example, determining optimal harvest time. In various configurations, a device of the present teachings used with associated methods, can be used to modify farming practices to enhance harvest yields.

In some configurations, the use of a device of the preset teachings can obviate the need to have personnel in the field present at the time of overflight collecting light measurements for post-hoc calibration. In some embodiments, the measurements described here can be bundled with other weather measurements within a single station. In some embodiments, a ground-based station of the present teachings can allow a crop adviser to make recommendations to a farmer, through remote collection of relevant data concerning weather and crop responses/crop growth. In some aspects, a ground-based station of the present teachings can further provide ground control for drone flights.

In some embodiments, a ground station of the present teachings can comprise at least two downward-facing light sensors which can collect radiation in narrow (<50 nm) spectral bands in the spectrum from about 400 to about 1100 nm, or from 400 nm to 1100 nm, at least one upward facing light sensor, a means to level the device, and a GPS. In some configurations, an upward facing light sensor can collect radiation in narrow (<50 nm) spectral bands contained in a wider spectral band such as a spectrum spanning about 400 to about 1100 nm, or 400 nm to 1100 nm. In various configurations, an upward facing light sensor can be a sensor which measures broadband radiation across the visible (about 400 to about 700 nm, or 400 nm to 700 nm) or both visible and NIR, (about 400 to about 1100 nm, or 400 nm to 1100 nm) spectrum. In sonic configurations, a light sensor can be an LED. In various configurations, a light sensor can measure light in a narrow spectral band. In some configurations, a narrowband sensor can be a broadband photodiode that can further comprise one or more filters that can filter out light outside a target spectral range. In some configurations, the means to level the device can be a bubble level or a digital level such as a magnetometer. In various configurations, a level can have a display on a ground station, or on a handheld device such as a mobile telephone which can communicate with the ground station, for example and without limitation, via BLUETOOTH® (BLUETOOTH® SIG, Kirkland, Wash.) wireless communication technology. In some configurations, a level can send the device pose to a remote server using onboard telemetry. In various embodiments, the GPS can have low intrinsic accuracy (greater than about 10 cm) but can be used to determine a position that can be accurate to within about 10 cm or less, or 10 cm or less. This accuracy can be determined by methods that include averaging a plurality of position readings collected over time. In art alternate configuration, the GPS can use differential correction to derive an instantaneous GPS reading with high accuracy (i.e., 10 cm or less). In some configurations, the device can further comprise a means to measure its height above the ground. In various configurations, the means to measure height can be a laser rangefinder, an acoustic rangefinder or a means to measure mean altitude above sea level (MASAL) such as, without limitation, a GPS. In some configurations, a station of the present teachings can be a single integrated unit comprising radiometric and positional sensors. In various configurations, a station can be a unit that combines a plurality of sensors into a single package. In various configurations, a sensor included in a device of the present teachings can be, in non-limiting example, a rain gauge, downwelling and upwelling longwave radiation sensors, an air temperature sensor, a humidity sensor, a pressure sensor, an imager, and a soil moisture sensor. In various configurations, a device of the present teachings can further comprise one or more additional sensors, such as a wind sensor, a humidity sensor, a heat sensor and a precipitation sensor. In various configurations, a device of the present teachings can further comprise one or more additional sensors, such as a rain gauge, downwelling and upwelling longwave radiation sensors, an air temperature sensor, a humidity sensor, a pressure sensor, an imager, and a soil moisture sensor. In some configurations, a station can further comprise a means for measuring the temperature at the surface of the device. In some configurations, the means for measuring the temperature at the surface of the device can comprise or consist thermocouple embedded in an enclosure of the device or thermistor embedded in an enclosure of the device.

In some embodiments, a station of the present teachings can comprise at least two downward-fazing LEDs configured for collecting radiation in narrow (<about 50 nm, or <50 nm) spectral bands in the spectrum from about 400 to about 1100 nm, or 400 nm to 1100 nm; at least two upward-facing LEDS; and a means to level the device. In some configurations, the station can be positioned into service in a precise set of coordinates using a GPS such as a high-accuracy GPS that is not a part of the device.

In some embodiments, a system for determining agricultural conditions can comprise a device of the present teachings and at least one aerial image of an area comprising the device. In sonic configurations, a system of the present teachings can comprise a device of the present teachings and at least one aerial image of an area comprising the device wherein the at least one aerial image can he an RGB color image or all infrared image. In various aspects, the device a two or more downward-facing LEDs configured to collect radiation in a spectral band of < about 50 nm in a range of about 400 to about 1100 nm, or 400 nm to 1100 nm, and two or more upward-facing LEDs configured to collect radiation in a spectral band of <50 nm in a range of about 400 nm to about 1100 nm, or 400 nm to 1100 nm.

In some embodiments, the present teachings include methods of providing qualitative and quantitative assessments of the state of vegetation for actionable decision support. In some embodiments, the present teachings include methods of post-processing remotely-sensed imagery, such as, but not limited to, imagery of a target area such as, without limitation, an agricultural region or a natural resource. In various configurations, these methods can comprise providing aerial images of an area using a digital camera carried by an airplane or drone. The imaging can be remotely sensed imagery (RSI), which can include RGB color images and/or infrared images such as, but not limited to, near infrared images such as false color near infrared (NIR-R-G) images. The methods can further include determining location coordinates for RSI data interpretation, and measuring upwelling and downwelling radiation within a defined spectral band. In various configurations, the methods can also include measuring and recording environmental parameters such as, without limitation, temperature, humidity, wind speed, and time of day. In various configurations, the upwelling and downwelling radiation can be determined using a device comprising light-sensitive light-emitting diodes (LEDs) as light sensors, and optical filters for limiting upwelling and downwelling radiation to specific wavelength ranges. In various configurations, the methods can include employing two or more downward-facing LEDs to collect radiation in a narrow (<about 50 nm) spectral band in the range of about 400 nm to about 1100 nm, or 400 nm to 1100 nm, and two or more upward-facing LEDs to collect radiation in a narrow (<50 nm) spectral band in the range of about 400 to about 1100 nm, or 400 nm to 1100 nm. In various configurations, the methods include employing LEDs which can detect broadband radiation across the visible (approx. 400 nm to approx. 700 nm, or 400 nm to 1100 nm) spectrum. In various configurations, the methods include employing LEDs that can detect broadband radiation across the visible (from about 400 nm to about 700 nm, or 400 nm to 700 nm) spectrum. In various configurations, the methods include employing LEDs that can detect broadband radiation across the near infrared (from about 800 nm to about 1100 nm, or 800 nm to 1100 nm) spectrum. In various configurations, the methods include employing LEDs that can detect broadband radiation across the visible plus near infrared (from about 400 nm to about 1100 nm, or 400 nm to 1100 nm) spectrum. In various configurations, the methods can include employing OEM components to measure light in a defined narrow band. In various configurations, the methods can include employing a broadband photodiode in combination with optical filters for cutting off light outside the target range. In various configurations, the methods can include measuring downwelling radiation in a narrow band (<50 nm) to compute reflectance. In various configurations, the methods can include measuring downwelling radiation in a broad band to compute reflectance, such as, for example, when the spectral distribution of solar radiation is assumed.

In some configurations, the methods can include determination of irradiance. In some configurations, these methods can include passing light through a diffuser to cosine correct radiation of the hemisphere. In some configurations, the methods of the present teachings can include determination of radiance. In these configurations, light can come from a solid angle less than a full hemisphere.

In various configurations, methods of the present teachings can include correction of imagery by retrospectively retrieving light, time of day, and position data of a target area for which RSI is collected. In some aspects, the methods include determining temperature of the device, for example through the use of a thermistor or thermocouple embedded in the device. In some aspects, the present teachings include methods of determining position of the device. These methods include collecting multiple GPS readings of position, and determining an average figure for position. In some configurations, the position of the device can be determined to an accuracy of about 10 cm or less using these methods.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1A:
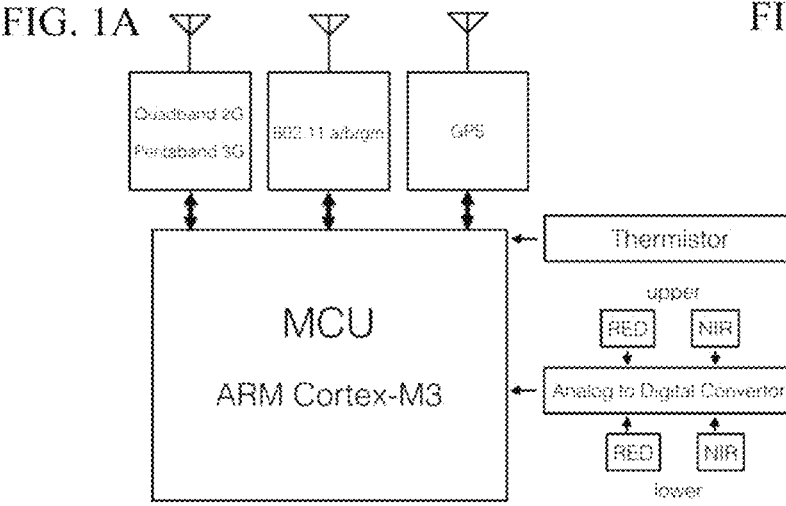
FIG. 1A-C depict block diagrams of a ground station of the present teachings.

As used in the present description and the appended claims, the singular forms "a", "an" and "the" are intended to include the plural forms as well, unless the context indicates otherwise.

The present inventors have developed a ground station for automation of gathering location coordinates and color measurements for RSI data interpretation. In various embodiments, a unit of the present teachings can be a stand-alone device or part of a weather station or similar device for the collection of other environmental data. In some configurations, a ground station of the present teachings can push collected data to a database via a standard communication system, such as, without limitation, a Wi-Fi link, a cellular uplink and/or on-board radio telemetry using other frequencies and communications protocols. In some configurations, the database can he accessed over the internet. In some configurations, data recorded using a device of the present teachings can be used in a method for post-processing remotely-sensed imagery, including imaging of agricultural and natural resources and the built environment. These data can allow an end user to view sequential RSI images in a time course progression with corrections for variations in ambient radiance, such as sunny or overcast conditions.

In various embodiments, a ground station of the present teachings can be the size of a single pixel in the RSI, or larger, and can be distinguishable in the image from the background below it by a distinct spectral signature, such as, for example, white or black in a green background. The size of a single pixel relative to the imaging equipment used for a given application would be apparent to a person of ordinary skill in the art.

In some configurations, a ground station of the present teachings can be attached to an imaging target that can be at least the size of single pixel in the RSI. The imaging target can be of an appearance that makes it distinguishable from the background of the RSI imaging, such as and without limitation, a white square or circle which can be deployed in the field against a background of green plants. The size of target required ran be dependent on the resolution of imaging for which it is being used. For example, but without limitation, when using high resolution (e.g., 1 cm) imaging a pixel can be 10-20 $cm^2$. However, if the ground station is smaller than the pixel, for example and without limitation, 10 $cm^2$ in an image where a pixel is 20 $cm^2$, then a target can be, for example, 25 $cm^2$ to 1 $m^2$. In some configurations, a ground station of the present teachings can use downward-facing light detection to measure an area wider than the device itself, so that pixels of the RSI that are adjacent to the image of the device can be used to calibrate the RSI. In some configurations, adjacent pixels can be selected to avoid shadows; such as selecting pixels to the south of the ground station if it is placed in the Northern hemisphere. In some embodiments, three or more ground bases can used in the same area to provide sufficient degrees of freedom to scale, rotate and translate the image into real world coordinates using an affine transformation.

In some embodiments, a ground station can comprise at least two downward facing LEDs which collect radiation in narrow (<50 nm) spectral bands within the spectrum between about 400 to about 1100 nm; at least one upward-facing LED which collects radiation in narrow (<50 nm) spectral bands in the spectrum between about 400 to about 1100 nm; a means to level the ground station such as a magnetometer, a bubble level or a combination thereof; and a GPS with accuracy equivalent to a single pixel in an RSI.

In some embodiments, the present teachings include a device for measuring light conditions at a location. In various configurations, a device can comprise; at least two downward facing collecting elements; at least one upward facing collecting element; and a leveling element. In some configurations, the device can further comprise a GPS. In some configurations, the collecting elements can collect narrow spectral bands from 400-1100 nm. In some configurations, the upward facing collecting elements can collect broadband radiation across a spectrum, such as, without limitation. 400-700 nm or 400-1100 nm. In some configurations, a collecting element can be an LED. In some configurations, a collecting element can be a broadband photodiode which can be combined with a pair of filters for cutting off light outside the target range. In various configurations, the leveling element can be a bubble level or a magnetometer. In some configurations, the GPS can be used to determine a fixed position accurately, to within about 10 cm, by repetitively measuring position, e.g., 1 measurement per hour over a week, with 20 or more independent measurements, for example hourly measurements over the course of 1 day or longer, and averaging the data. In various configurations. stations that do not carry on-board GPS can be placed using a GPS with 10 cm accuracy so that the position can be known with sufficient accuracy for subsequent imaging.

In various configurations, the GPS can use differential correction to determine location. In some configurations, a device of the present teachings can further comprise a means to measure the device's height relative to the ground. In various configurations, a means to measure the device's height relative to the ground can be, for example and without limitation, a laser rangefinder or an acoustic rangefinder. In some configurations, a device of the present teachings can further comprise a means to report the device's mean altitude above sea level. In some configurations, the means to report the device's mean altitude above sea level can be a GPS. In some configurations, a device of the present teachings can be a single unit. In various configurations, the device can comprise a plurality of sensors. The plurality of sensors can comprise or consist of, wind sensors, humidity sensors, and precipitation gauges. In various configurations, the plurality of sensors can comprise a rain gauge, downwelling and upwelling longwave radiation sensors such as, without limitation, LED sensors, an air temperature sensor, such as, without limitation, a thermometer, a humidity sensor, such as, without limitation a hygrometer, a pressure sensor, such as and without limitation a barometer, an imager, such as and without limitation a camera, and a soil moisture sensor.

In various configurations, a station of the present teachings can include a variety of LEDs. Non-limiting examples of LEDs that can be used to measure specific spectral bands include VISHAY® (VISHAY INTERTECHNOLOGY INC®, Malvern, Pa.) model BSMG 2700 which measures $\lambda_{peak}$ 830 nm and VISHAY® model BLMD3100 which measures $\lambda_{peak}$ 650 nm. A non limiting example of an LED that can be used for broadband detection is Hamamatsu GaAsP photodiode G1118 (Hamamatsu Photonics, Middlesex, N.J.) which reads a $\lambda_{range}$ 400-700 nm. A person of ordinary skill in the art will appreciate that a variety of comparable LEDs can be used in accordance with the present teachings.

Figure 1B:
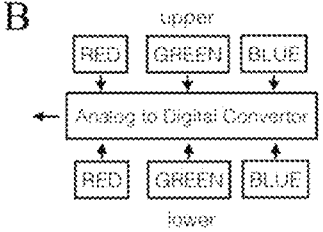
Figure 1C:
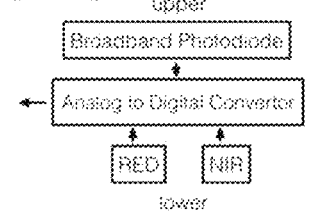

Block diagrams of various configurations of a ground station of the present teachings are depicted in FIG. 1A-C. FIG. 1A, depicts a central processor (MCU) connected to a communications chip which contain software that allows the ground station to make use of cellular signals such as, without limitation, 2G, 3G, or 4G LTE (this chip is labeled "Quadband 2G, Pentaband 2G" in the block diagram), a GPS for collecting position information, a thermistor for monitoring the surface temperature of the device, and an analog to digital converter to measure current from LEDs as spectral measurements of red and near infrared (NIR) light from above and below the ground station. Each block represents a separate LED. FIG. 1B depicts a variant of the LEDs connected to the analog to digital converter (the remaining components are the same as FIG. 1A) that measures red/green/blue light instead of red and NIR. FIG. 1C depicts a third configuration that uses a broadband light measurement of downwelling radiation, and narrowband spectral measurements of upwelling radiation from LEDs.

EXAMPLES

The present teachings including descriptions provided in the Examples that are not intended to limit the scope of any claim or aspect. Unless specifically presented in the past tense, an example can be a prophetic or an actual example. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Example 1

Figure 2:
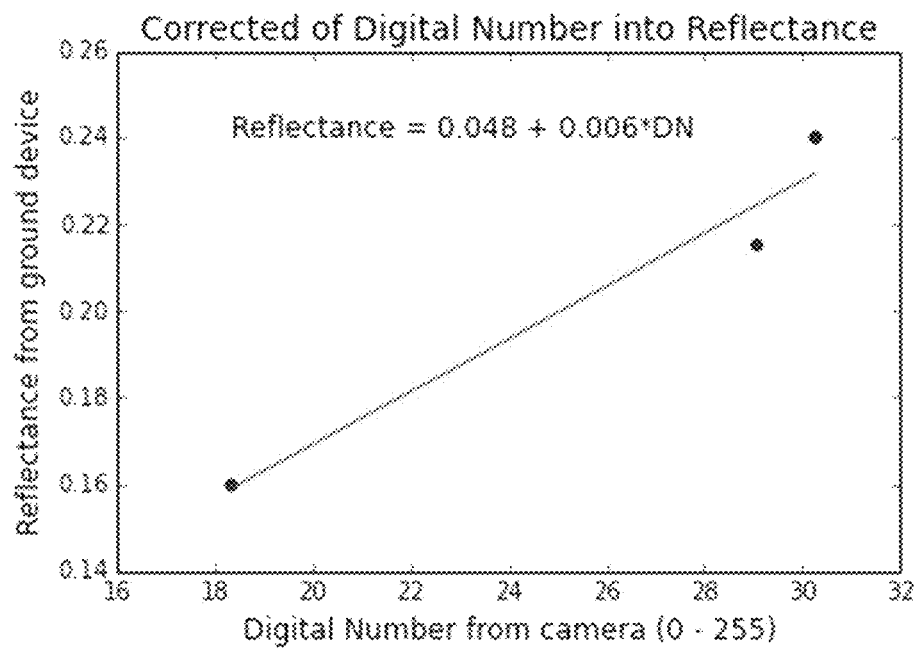
FIG. 2 depicts a linear regression analysis used to calculate reflectance from radiance measurements.
Figure 3:
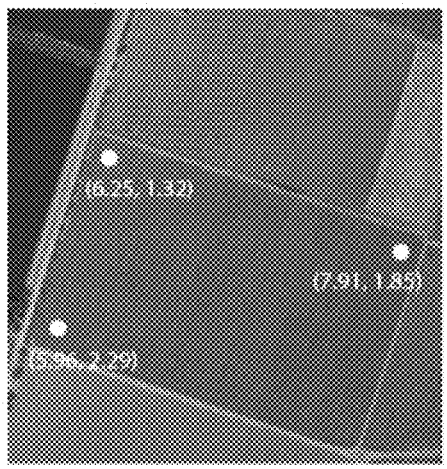
FIG. 3 depicts an aerial photograph with white dots drawn in to represent ground stations of the present teachings.
Figure 3:
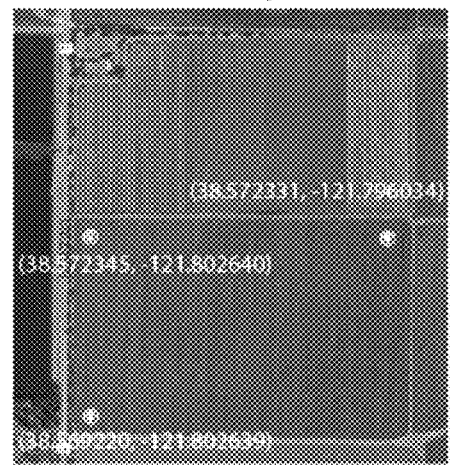

Three white ground stations of the present teachings are installed in a farmer's field in San Louis Obispo, Calif. (in the Northern hemisphere) and record continuous readings of upwelling and downwelling radiation data while a camera mounted in a drone collects remotely sensed imagery (RSI). The RSI includes standard RGB color images. Data collected by the devices and the RSI images are downloaded to a remote server located in a drone control center. The radiometric data (in the form of digital numbers, 8-bits for each channel) are then processed into reflectance measurements (FIG. 2): For each ground station, the pixels in the RSI that contain the device are identified by searching for the white ground stations amongst the green in the field (FIG. 3, left). The identification of the ground stations is accelerated using prior knowledge of their coordinates (FIG. 3, right), along with GPS metadata embedded in the image, to localize the search area within the RSI. Additionally, the spectral signature of each device is used to assign a contrast measure to it, which accelerates the search by prioritizing checking pixels that stand out against the target background. A non-shadowed pixel adjacent to, but not including, the device is selected. Using the radiometric data from each of the three ground stations, a regression analysis between the radiance data from the drone and the reflectance data from each ground station is performed (FIG. 2). The slope-intercept of the regression analysis is then used in the pixels without ground stations of the present teachings to color correct the RSI: A pixel near the ground station at (6.25., 1.32) has a digital value of 22, the reflectance is therefore 0.048+0.006×22=0.18. This radiometric correction is performed for each spectral band being analyzed at each pixel to normalize the image to the ambient lighting conditions. After color-correcting each individual image, the group of images are mosaicked into a single image using PhotoScan by Agisoft (St. Petersberg, Russia).

The mosaicked image is then converted from (X, Y) image coordinates into real-world (latitude, longitude) coordinates using an of ne transformation (FIG. 3). The ground station in the upper right of FIG. 3 has image coordinates of X=6.25, Y=1.32, which are known to correspond to 35.572345 N latitude, −121.802640 W longitude. These known coordinates are based on the GPS coordinates of the ground-based station, which are regarded as "ground truth". The known positions in the maps are then translated to the remainder of the image via affine transformation:

$$\vec{y} = A\vec{x} + \vec{b} .tm \quad [Eq. 1]$$

where x is a vector representing the original (x,y) position, y is a vector representing the transformed (x.y) position, and A and b are a matrix and vector respectively containing coefficients for performing the transformation. This position—and brightness—corrected image is then provided to a crop advisor. The crop advisor then uses the corrected image and associated data to calculate the NDVI for each pixel. For example, in a pixel at 35.572347 N latitude, −121.802641 West longitude, the red reflectance is 0.1 and the IR reflectance is 0.8. The NOVI is calculated as: NDVI=(0.8−0.1)/(0.8+0.1)=0.77. This is repeated over all adjacent pixels, and found to be consistent in the western half of the field. In this section of the field, the NDVI is therefore in the bottom quantile (<0.4) a values for the entire field, indicating an unusual amount of stress. On the crop adviser's recommendation, the farmer performs a physical examination of that section of the field, which reveals a fault in the irrigation line which is then repaired.

Example 2

Five ground stations of the present teachings are installed in a farmer's field in. Australia (in the Southern hemisphere) and record continuous readings of upwelling and down welling radiation collect digital numbers of 8 bits, per color channel while a drone collects remotely sensed imagery (RSI). The RSI includes standard false color infrared (NIR-R-G) images. Data collected by the devices and the RSI images are downloaded to a remote server. A regression analysis between the radiance data from the drone and the reflectance data from each ground station is performed. The equation Reflectance=0.37+0.004*DN, calculated from this linear regression, is used, using pixels from the Northern side of the device to avoid shadows. A pixel near one of the ground stations has an upwelling radiance of 27, and its reflectance is calculated using 0.37+0.004*27=0.478. The pixels in the RSI that contain the device are identified by its distinct spectral signature, and mosaicked RSI are transformed into real world coordinates, one ground station is located at −28.916960 latitude 153.154689 longitude, which is visually identified at 2.2, 4.3 in the image. These correspondences are used for each of the ground devices with the known coordinates and an affine transformation is used to determine the real world coordinates for the entire image. A position-corrected false color ortho-mosaic image is then provided to a crop advisor. The crop advisor then calculates the NDVI for each pixel, which has a median value of 0.8 in three quarters of the field, but the Northeast quadrant of the field has an NDVI of 0.72-10% lower than the rest of the field. After physical inspection of this quadrant, the crop advisor recommends that in subsequent years the fanner reduce the seeding density of the field from 20,000 seeds per acre to 18,000 seeds per acre in that part of the field.

Example 3

A cranberry farm manager in New Jersey hires a drone operator to take aerial photographs for a growing season, using a sensor that records thermal images. Several ground stations (numbered one through seven) of the present teachings are installed in the field. The position, radiance and irradiance along with infrared thermometer readings are pushed to a database over a cellular network. The drone operator provides the imagery to the client via a web interface. The farm manager logs in securely to the database, and calculates the difference between the temperature calculated from the infrared thermometer readings collected by the ground station and the temperature for the same location measured in the drone-collected imagery. The RSI reading at Ground Station One's pixel is 22.6° C. while the ground station infrared thermometer has a reading of 23.2° C. at the time of image capture, so the difference is 0.6° C. and adjusts the thermal image by this difference using equation: Calibrated T=Image T−0.6° C. These images are taken every two weeks. On the second round of images, the northern half of the Southeast quadrant of the field has a median temperature of 27°, a 5° increase relative to previous images and the rest of the field, accounting for ambient weather conditions. A physical inspection of the plants in that area reveals that the plants have phytopthora root disease, and the plants are sprayed to kill the mold.

Example 4

A farm manager in Missouri hires a drone operator to take aerial photographs that are visible light (R-G-B) for a growing season. Four ground stations of the present teachings are installed in the field. The position, radiance and irradiance are pushed to a database over a cellular network. An agricultural adviser logs in to the database securely. The radiometric data, digital numbers with 8 bits for each channel, are then processed into reflectance measurements. Pixels in the RSI that contain the device are identified by searching for the white ground stations amongst the green in the field. The identification of the ground stations is accelerated using prior knowledge of their coordinates, along with GPS metadata embedded in the image, to localize the search area within the RSI. Additionally, the spectral signature of each device is used to assign a contrast measure to it, which accelerates the search by prioritizing checking pixels that stand out against the target background. A non-shadowed pixel adjacent to, hut not including, the device is selected. Using the radiometric data from each of the three ground stations, a regression analysis between the radiance data from the drone and the reflectance data from each ground station is performed. The slope-intercept of the regression analysis is then used in the pixels without ground stations of the present teachings to color correct the RSI: A pixel near the ground station at (6.3, 2.15) has a radiance of 25; the reflectance is therefore 0.33+0.007*25=0.505. This radiometric correction is performed for each spectral band being analyzed at each pixel to normalize the image to the ambient lighting conditions. After color-correcting each individual image, the group of images are mosaicked into a single image using Phot Scan by Agisoft (St. Petersberg, Russia).

The mosaicked image is then converted from (X, Y) image coordinates into real world (latitude, longitude) coordinates using an affine transformation. For example, the ground station in the upper right of the field has image coordinates of X=4.3 Y=18.2 which is known to correspond to 37.968944, −91.655015. These known coordinates are based on the GPS coordinates of the ground-based station, which are regarded as "ground truth." The known positions in the maps are then translated to the remainder of the image using an affine transformation. This position- and brightness-corrected image is then used to calculate the VARI-green index (G−R)/(G+R−B) for each pixel in the images with a median of 0.72 over the field, and determines that one section of field has a VARIgreen index, 0.57, which is 20% lower than the rest of the field. The agricultural, advisor recommends that the farm manager use 40 fewer kilograms of nitrogen per acre for this section of the field.

Example 5

Four black ground stations of the present teachings, installed in a farmer's field in Nebraska (in the Northern hemisphere), record continuous readings of upwelling and downwelling radiation while a camera mounted in a drone collects remotely sensed imagery (RSI). The RSI includes standard RGB color images. Data collected by the devices and the RSI images are downloaded to a remote server. The radiometric data are then processed into reflectance measurements. For each ground station, the pixels in the RSI that contain the device are identified by searching for the black ground stations amongst the green in the field. The identification of the ground stations is accelerated using prior knowledge of their coordinates, along with GPS metadata embedded in the image, to localize the search area within the RSI. Additionally, the spectral signature of each device is used to assign a contrast measure to it, which accelerates the search by prioritizing checking pixels that stand out against the target background. A non shadowed pixel adjacent to, but not including, the device is selected. Using the radiometric data from each of the four ground stations, a regression analysis between the radiance data from the drone and the reflectance data from the RSI is performed. The slope-intercept of the regression analysis is then used in the pixels without ground stations of the present teachings to color correct the RSI, for example the pixel just South of a ground station has a reflectance of 24, the slope of the regression is 0.003, and the intercept is 0.35, so the reflectance would be calculated as 0.35+0.003*24=0.422. This analysis is performed for each spectral band being analyzed. This image is therefore normalized to the ambient lighting conditions. After color-correcting each individual image, the group of images arc mosaicked into a single image using PhotoScan Agisoft (St. Petersberg, Russia).

The mosaicked image is then converted from (X, Y) image coordinates into real-world (latitude, longitude) coordinates using an affine transformation. For example, the ground station in the upper right of the field has image coordinates of X=12.7, Y=3.2, which is known to correspond to 41.827026, −97.065104. These known coordinates are based on the GPS coordinates of the ground-based station., which are regarded as "ground truth". The known positions in the maps are then translated to the remainder of the image using an affine transformation (Eq. 1). This position- and brightness-corrected image is then provided to a crop adviser. The crop adviser then uses the corrected image and associated data to calculate the NDVI for each pixel, which has a median of 0.59 for the field. The crop advisor uses the NDVI to determine the amount of crop biomass by the method of Wang, J., et al., Geocarto. International, Vol. 20, No. 3, September 2005, and then uses this to update process-based crop model-derived yield predictions for each square meter of field. Replacing model-predicted crop biomass with RS-estimated crop biomass in the yield predictions allows the farmer to negotiate an advance contract for the predicted crop yield, at a favorable price on the commodities market.

Example 6

Three small ground stations of the present teachings, (in which each station image is smaller than a single pixel), each of which has a large, white target affixed to it, are installed in a farmer's field in Fresno, Calif. (in the Northern hemisphere). The devices record continuous readings of upwelling and downwelling radiation while a camera mounted in a drone collects remotely sensed imagery (RSI). The RSI includes standard RGB color images of 8 bits per channel. Data collected by the devices and the RSI images are downloaded to a remote server. The radiometric data are then processed into reflectance measurements. For each ground station, the pixels in the RSI that contain the device are identified by searching for the white ground stations amongst the green in the field. The identification of the ground stations is accelerated using prior knowledge of their coordinates, along with GPS metadata embedded in the image, to localize the search area within the RSI. Additionally, the spectral signature of each device is used to assign a contrast measure to it, which accelerates the search by prioritizing checking pixels that stand out against the target background. A non-shadowed pixel adjacent to, but not including, the device is selected. Using the radiometric data from each of the four ground stations, a regression analysis between the radiance data from the drone and the reflectance data from the RSI is performed. The slope-intercept of the regression analysis is then used in the pixels without ground stations of the present teachings to color correct the RSI, for example the pixel just north of a ground station has a reflectance of 29, the slope of the regression is 0.005, and the intercept is 0.45, so the reflectance would be calculated as 0.45+0.005*29=0.595. this analysis is performed for each spectral band being analyzed. This image is therefore normalized to the ambient lighting conditions. After color-correcting each individual image, the group of images are mosaicked into a single image using PhotoScan by Agisoft (St. Petersberg, Russia). The mosaicked image is then converted from (X, Y) image coordinates into real-world (latitude, longitude) coordinates using an affine transformation. For example, the ground station in the upper right of the field has image coordinates of 5.4, Y=19.3, which is known to correspond to 36.687886, −119,883156. These known coordinates are based on the GPS coordinates of the ground-based station, which are regarded as "ground truth". The known positions in the maps are then translated to the remainder of the image by affine transformation (Eq. 1). This position- and brightness-corrected image is then provided to a crop adviser. NDVI variation in the field reveals bands of high crop productivity (NDVI=0.8) and bands of average productivity (NDVI=0.6), indicating that fertilizer application was most likely double-applied on areas where there was sprayer overlap. This represents an unnecessary cost that can be addressed by changing the application pattern or adjusting spray valves.

Example 7

This example illustrates use of a device of the present teachings to determine the effect of temperature on strawberry maturation.

Figure 4:
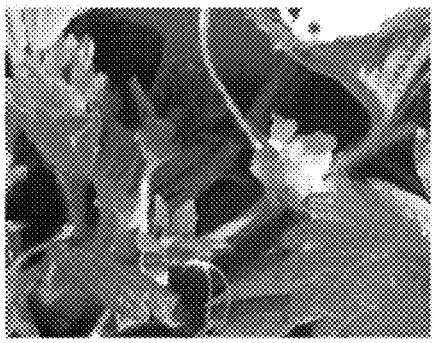
FIG. 4 depicts the stages of strawberry maturation.
Figure 4:
Figure 4:
Figure 5:
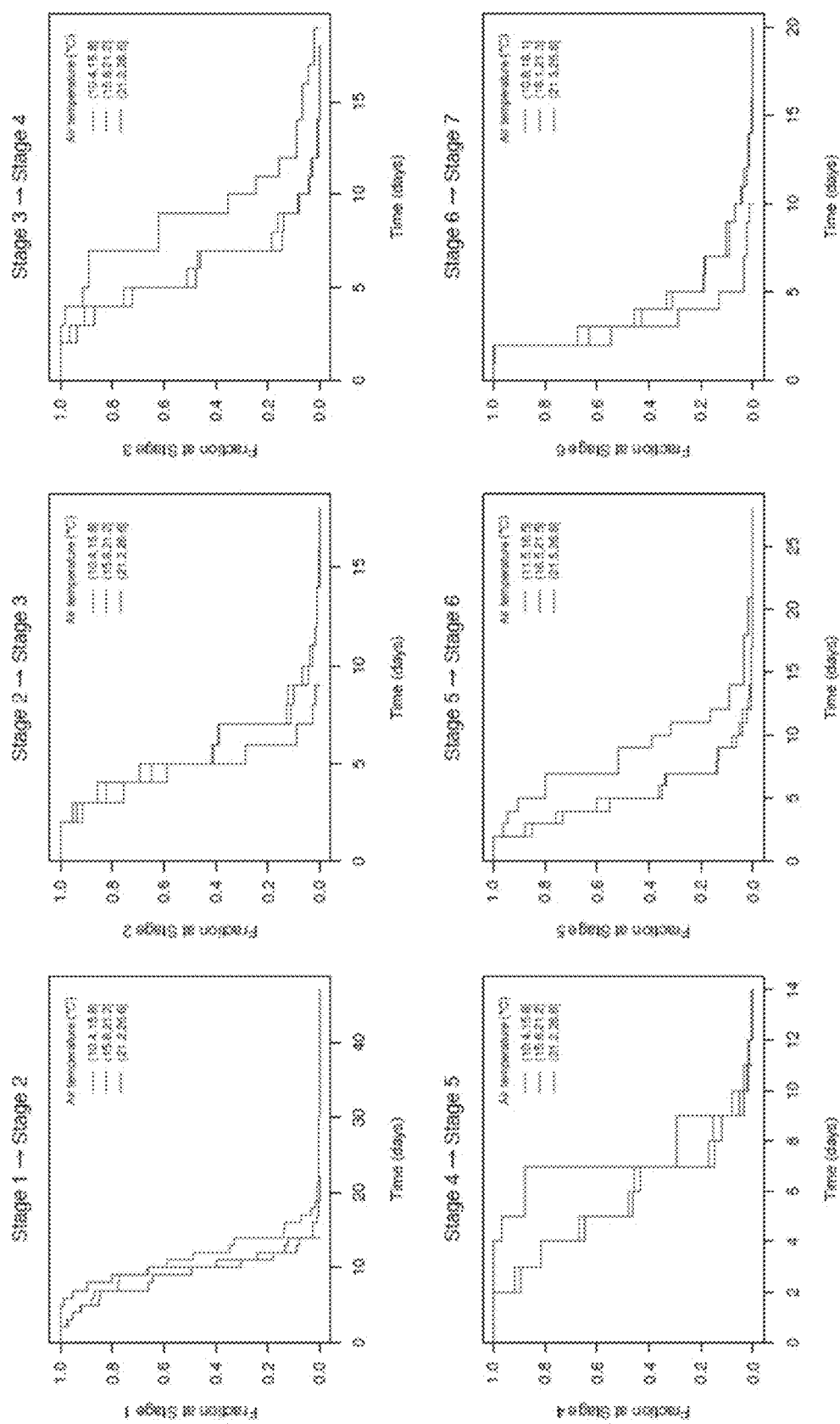
FIG. 5 depicts graphs of the maturation rate of berries split up by ambient air temperature.
Figure 6:
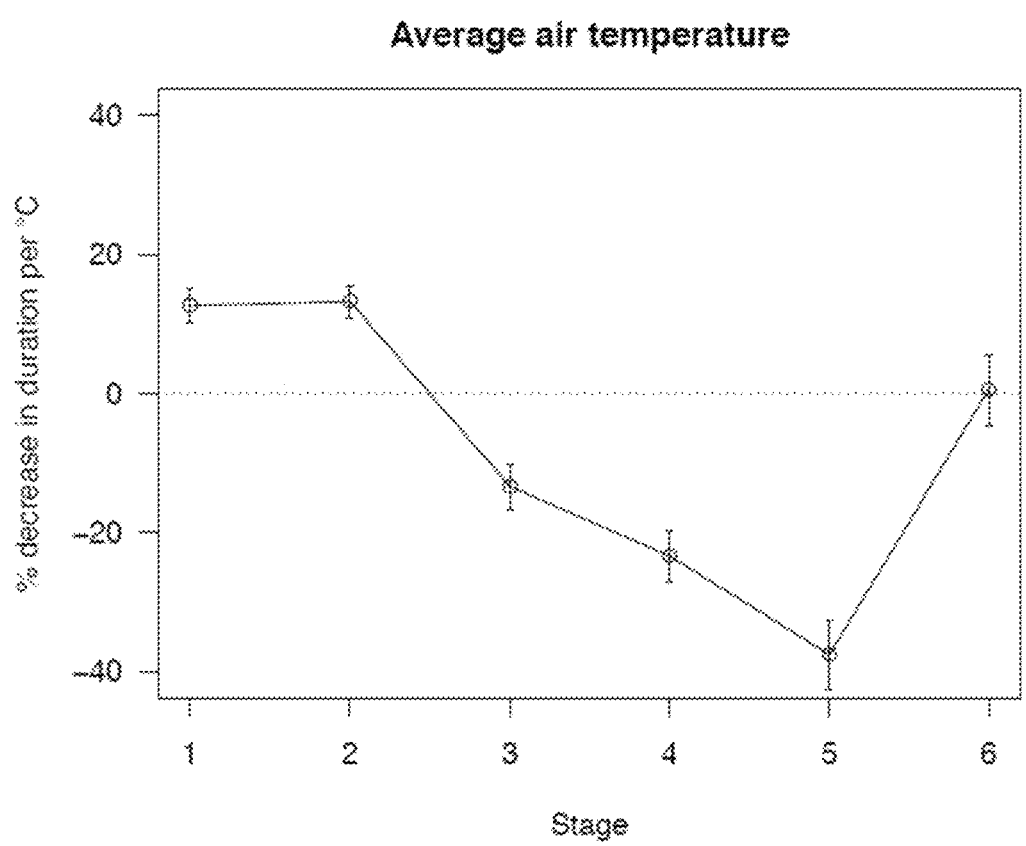
FIG. 6 depicts the percent decrease in maturation duration per ° C. at each stage of maturation.

Two devices of the present teachings were installed in two strawberry fields in Watsonville, Calif. and Salinas, Calif. The devices were used to measure the air temperature, and then berries were observed at various stages of maturation in accordance with FIG. 4. The air temperature readings were then broken into three ranges; 10.4-15.8° C., 15.8-21.2° C., and 21.2-26.6° C. For each stage transition, each air temperature range was then plotted for the time at each temperature against the fraction of berries still at the previous stage (FIG. 5). For example, the Stage 1 to Stage 2 transition was observed as time against the fraction of berries remaining at stage 1. Contrary to conventional wisdom, cooler air temperature were associated with faster berry maturation. This trend is more evident when average air temperature is plotted for each stage as a % decrease in duration per ° C. (FIG. 6), Without being limited by theory, berry expansion may be delayed by reduced turgor (a function of evaporative demand and soil moisture).

Example 8

This example illustrates use of a device of the present teachings to monitor crop health.

Figure 7:
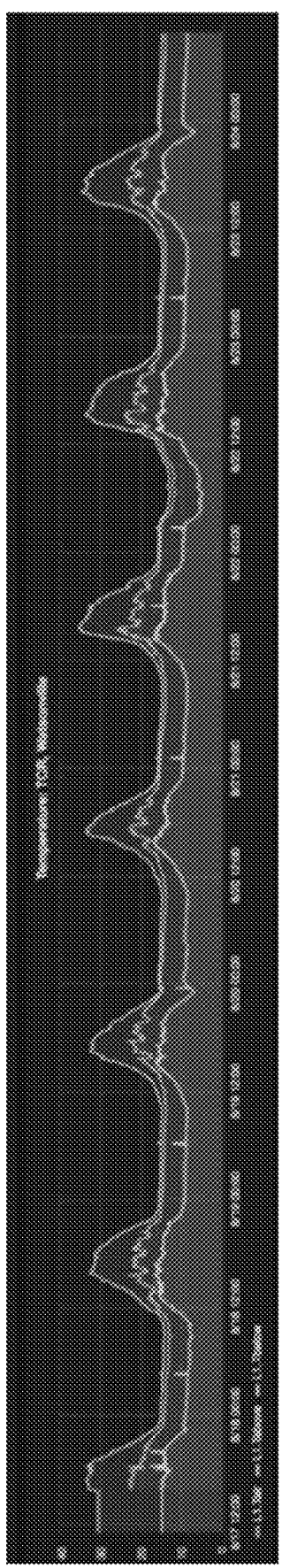
FIG. 7 depicts air temperature readings collected by a device of the present teachings in a strawberry field.

FIG. 7 illustrates real time temperature readings for weather stations of the present teachings installed in Salinas, Calif. as described in example 7. In this figure, yellow indicates the sky temperature, blue indicates the temperature of the plants, and green represents the air temperature. These data illustrate that the plant temperature was significantly higher than that of the air temperature. In healthy plants, these two readings should be the same. These data therefore indicate plant stress.

Example 9

Figure 8:
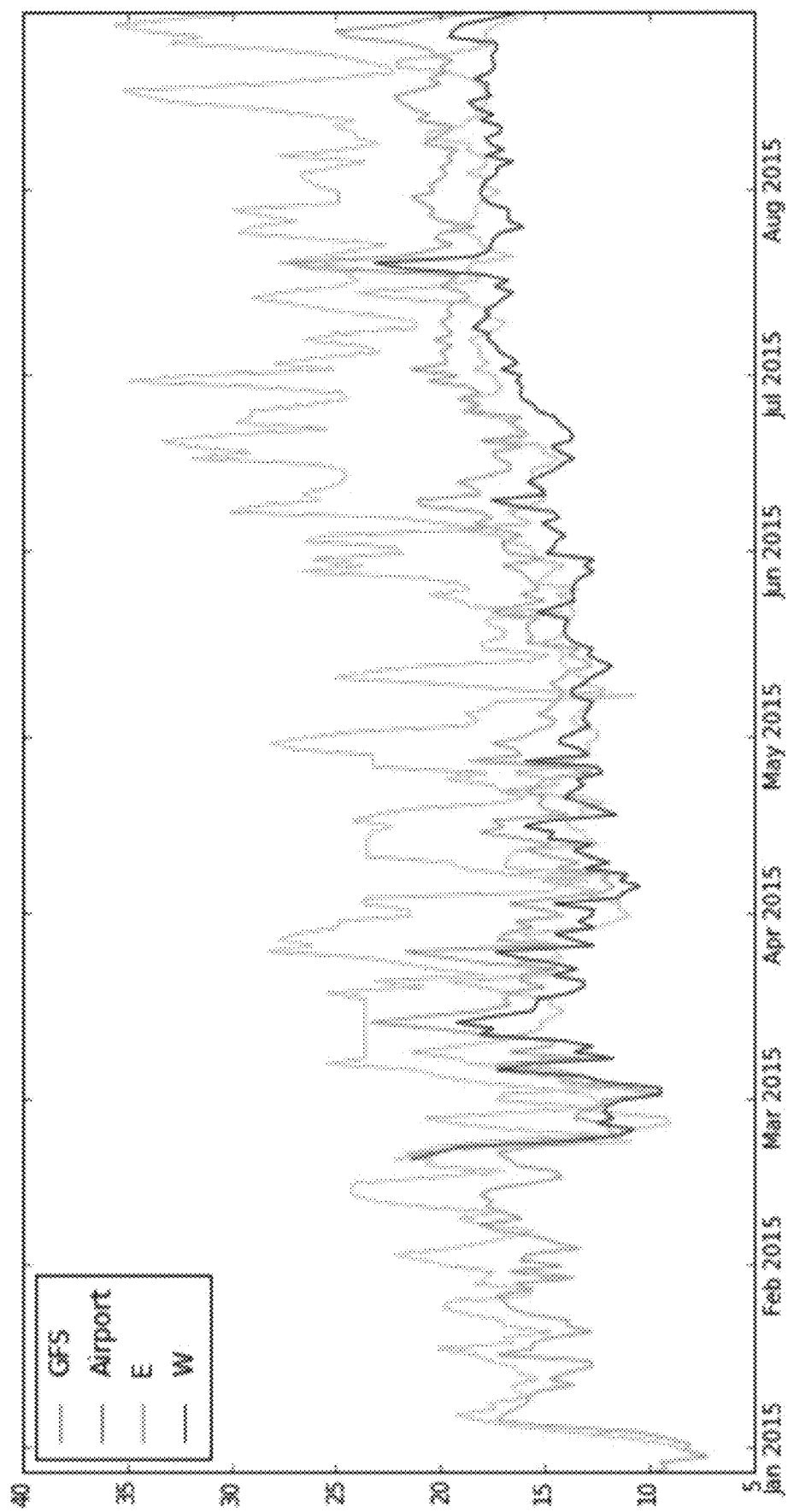
FIG. 8 depicts downscaled microclimate data at various locations a short distance apart.
Figure 9:
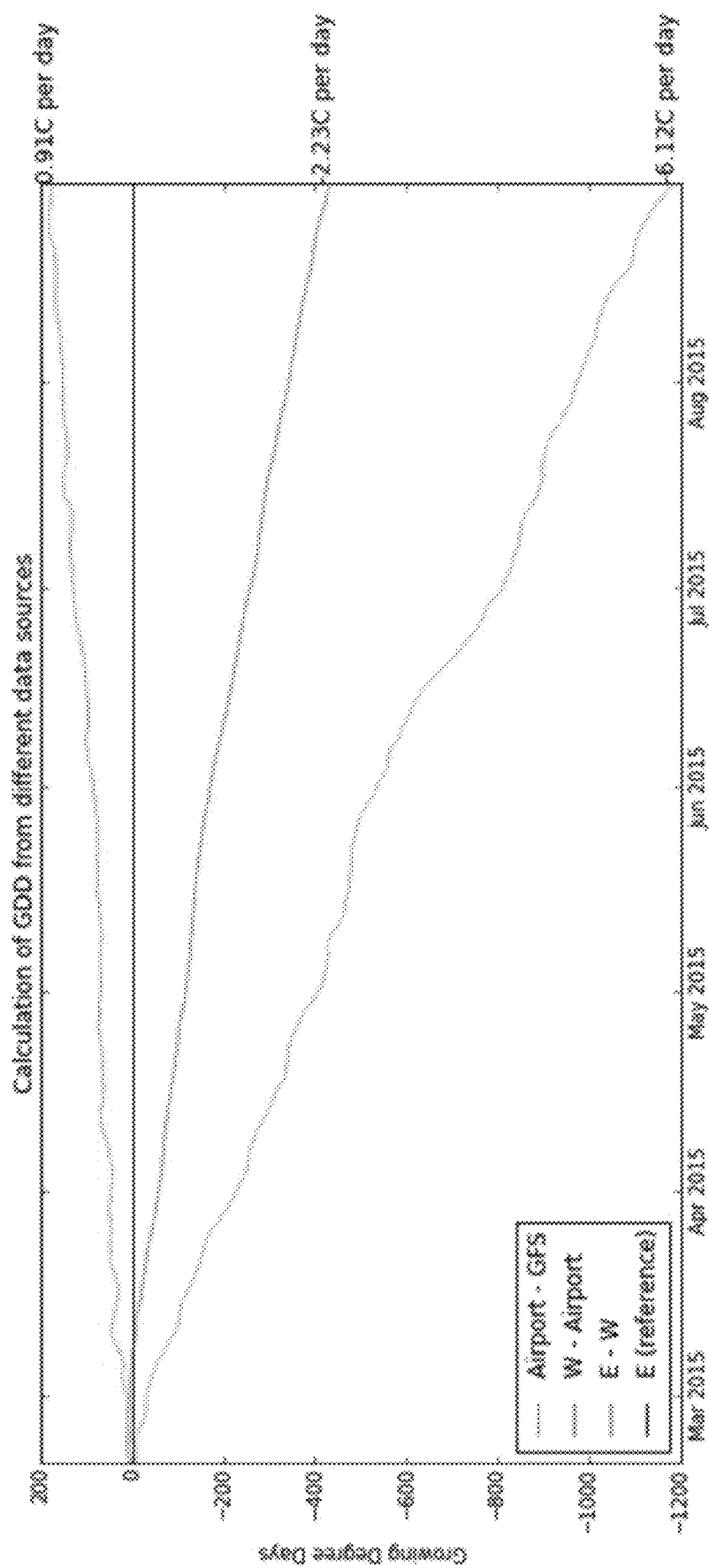
FIG. 9 illustrates that variations across short distances are sufficient to affect berry maturation rate by 20%.

This example illustrates the use of a device of the present teachings to observe changes in downscaled microclimate that increase the accuracy of scientific predictions, Devices of the present teachings were installed in two fields. E (orange) and W (blue), and used to measure air temperature over time. When plotted against readings taken by an NOAA weather station (GFS, grey) and readings taken at the local Airport (red), these data revealed that climate can vary by as much as 10° C. between microenvironments (FIG. 8). These differences, when plotted, showed that variations even across such short distances are enough to affect berry maturation rate by as much as 20% (FIG. 9).

Figure 10:
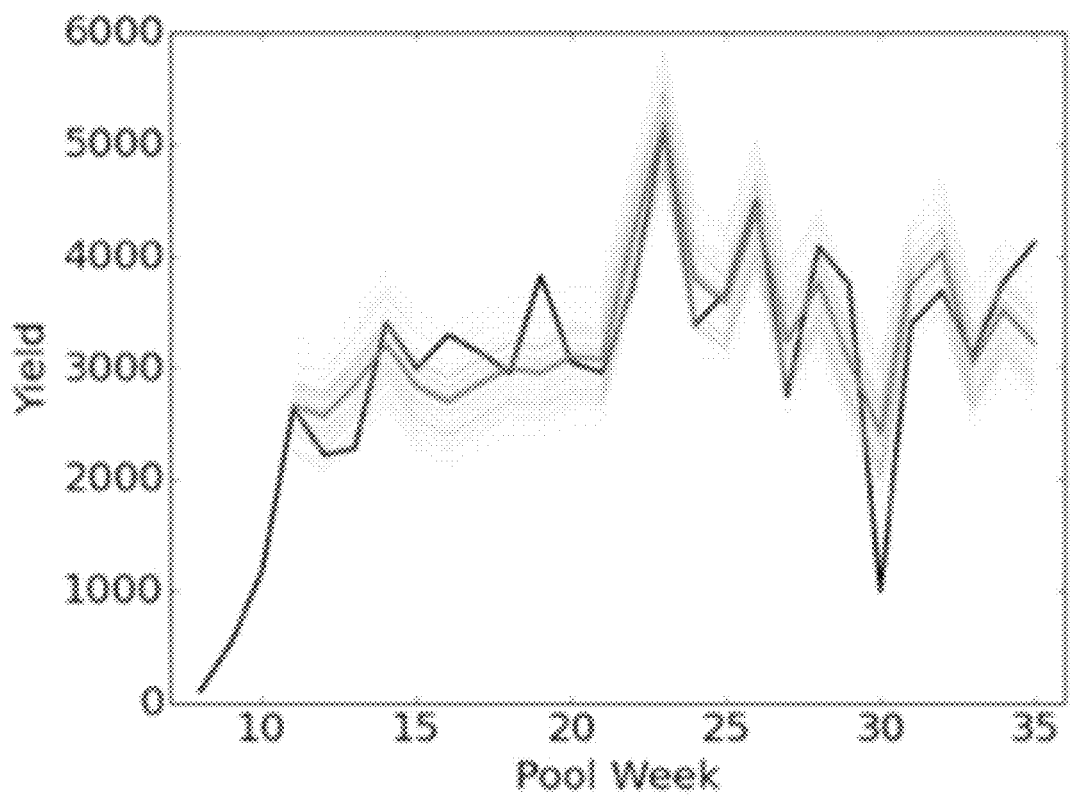
FIG. 10 illustrates predicted vs. actual yield in strawberry fields.

FIG. 10 shows the yield over time for several strawberry fields where test devices were installed. Red shows predicted yield using data from devices of the present teachings, black shows actual yield, and grey shows yield predicted using traditional methods. Using traditional methods, predictions show errors from 10-20% and leading indicators used in conventional practice have no statistically predictive power ($R^2$=0.002). However, using the temperature data, as described in examples 7-9, the predictions have errors within 5% ($R^2$0.62). These predictions are therefore more accurate than those using traditional methods.

Example 10

This example illustrates the use of a device in the present teachings in providing information for agricultural decisions.

A strawberry farmer installs a device of the present teachings into her strawberry field. Each week, she cheeks the relative crop temperatures from her dashboard at the data retrieval portal. In August, she is confronted with data similar to that in FIG. 7. Inspection of the crops does not reveal any signs of disease, so she increases the irrigation of the crops to better improve turgor pressure.

Example 11

This example illustrates the use of data provided by a device of the present teachings to manage strawberry crops.

A farm manager installs a device of the present teachings in a strawberry field. Based upon measurements collected by the device, the farm manager determines that the average temperature in the field is 5° C. less than normal for that time year over a week. The farm manager realizes that the berries will mature more rapidly than initially expected and reallocates crates and labor for harvest.

Example 12

This example illustrates use of a device of the present teachings to monitor disease risk.

Figure 11:
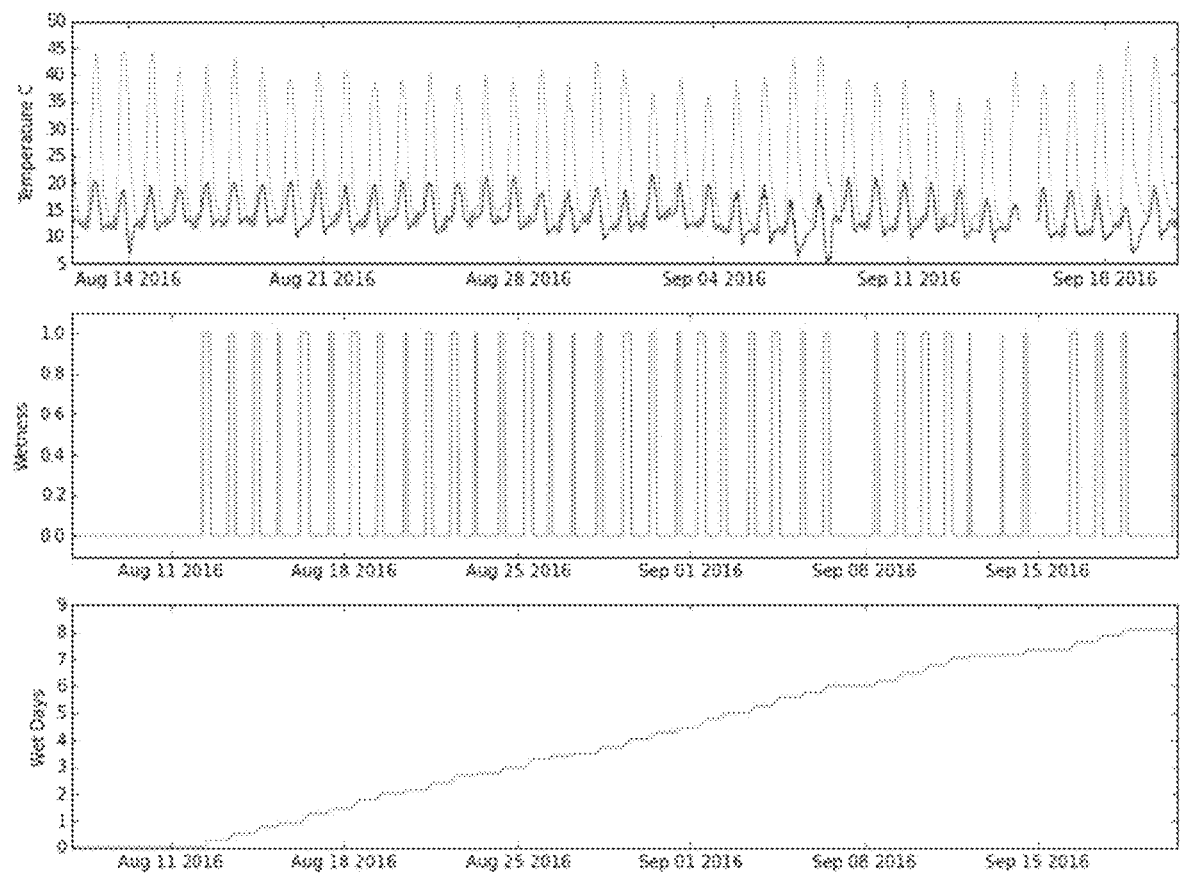
FIG. 11 illustrates temperature of plant leaves, and dewpoint temperature at the given atmospheric humidity, temperature, and pressure for weather stations of the present teachings.

FIG. 11 illustrates temperature of plant leaves, and dewpoint temperature at the given atmospheric humidity, temperature, and pressure for weather stations of the present teachings installed in Napa, Calif. In the upper figure, gray represents the temperature of the plants, blue represents the dewpoint temperature, and red represents times when the leaves are apparently at the dewpoint temperature. These data illustrate that in many periods, the leaves are at or below the dewpoint and therefore have condensation present on the leaves. Using a model of powdery mildew susceptibility (Thomas, C. S., Gubler, W. D., and Leavitt, G. 1994. Field testing of a powdery mildew disease forecast model on grapes in California. Phytopathology 84:1070), an advisor calculates the risk of powdery mildew presence by adding up the accumulated time of leaf wetness within certain temperature thresholds (bottom figure). Based on these calculations an advisor recommends an application of sulfite dust.

All publications cited herein are hereby incorporated by reference, each in its entirety.

What is claimed is:

1. A system for determining agricultural conditions, the system comprising:
   a stationary ground station installed at a location, the stationary ground station comprising:
   at least one first collecting element configured to measure upwelling radiation,
   at least one second collecting element configured to measure downwelling radiation,
   a leveling element, and
   a GPS receiver configured to generate location coordinates corresponding to a fixed position of the stationary ground station; and
   an analysis server comprising a processor executing instructions stored in memory, wherein the instructions cause the processor of the analysis server to:
   receive remotely sensed imagery of an area in which the stationary ground station is installed, the remotely sensed imagery comprises radiance data,
   receive the location coordinates from the stationary ground station,
   receive radiometric data from the stationary ground station, the radiometric data indicative of the upwelling radiation and the downwelling radiation measured by the first and second collecting elements,
   generate color-corrected imagery as a function of the radiance data of the remotely sensed imagery and the radiometric data received from the stationary ground station, and
   generate a mosaic image of the area based at least in part on the color-corrected imagery and the fixed position of the stationary ground station.

2. The system of claim 1, wherein the at least one first collecting element is at least two first collecting elements.

3. The system of claim 1, wherein each collecting element collects radiation in a spectral band of <50 nm in a range of about 400 to about 1100 nm.

4. The system of claim 1, wherein the at least one second collecting element collects broadband radiation across a spectrum selected from a group consisting of 400-700 nm and 400-1100 nm.

5. The system of claim 1, wherein each collecting element is an LED.

6. The system of claim 5, wherein the LED is a broadband photodiode.

7. The system of claim 6, wherein each collecting element further comprises a spectral filter.

8. The system of claim 1, wherein the leveling element is selected from a group consisting of a bubble level, a magnetometer, and a combination thereof.

9. The system of claim 1, wherein the stationary ground station further comprises a means for measuring a height of the stationary ground station relative to the ground.

10. The system of claim 9, wherein the means to measure the height of the stationary ground station relative to the ground is selected from a group consisting of a laser rangefinder, an acoustic rangefinder, and a combination thereof.

11. The system of claim 1, wherein the stationary ground station further comprises a means to measure a mean altitude above sea level of the stationary ground station.

12. The system of claim 11, wherein the means to measure the mean altitude above sea level of the stationary ground station comprises the GPS receiver.

13. The system of claim 1, wherein the stationary ground station further comprises one or more additional sensors, each additional sensor selected from a group consisting of a wind sensor, a humidity sensor, a temperature sensor, and a precipitation sensor.

14. The system of claim 1, wherein the remotely sensed imagery is collected by a satellite, an airplane, or a drone.

15. The system of claim 1, wherein the stationary ground station further comprises one or more additional sensors, each additional sensor selected from a group consisting of a rain gauge, a downwelling longwave radiation sensor, an upwelling longwave radiation sensor, an air temperature sensor, a humidity sensor, a pressure sensor, an imager, and a soil moisture sensor.

16. The system of claim 1, wherein the stationary ground station further comprises a communication system.

17. The system of claim 16, wherein the communication system is selected from a group consisting of a Wi-Fi link, a cellular uplink, an on-board radio telemetry, and combinations thereof.

18. The system of claim 1, wherein the stationary ground station further comprises an imaging target having an area of at least 10 cm$^2$.

19. A system for determining agricultural conditions, the system comprising:
   an analysis server comprising a processor executing instructions stored in memory, wherein the instructions cause the processor of the analysis server to:
   receive remotely sensed imagery of an area in which a stationary ground station is installed, the remotely sensed imagery comprises radiance data,
   receive location coordinates from the stationary ground station, the location coordinates correspond to a fixed position of the stationary ground station,
   receive radiometric data from the stationary ground station, the radiometric data indicative of upwelling radiation and downwelling radiation measured by the stationary ground station, generate color-corrected imagery as a function of the radiance data of the remotely sensed imagery and the radiometric data received from the stationary ground station, and generate a mosaic image of the area based at least in part on the color-corrected imagery and the fixed position of the stationary ground station.

20. The system of claim 19, wherein the remotely sensed imagery is selected from a group consisting of RGB color imagery and infrared imagery.

21. The system of claim 19, further comprising:
a stationary ground station installed at a location, the stationary ground station comprising:
at least one first collecting element configured to measure upwelling radiation,
at least one second collecting element configured to measure downwelling radiation, and
a GPS receiver configured to generate location coordinates corresponding to the fixed position of the stationary ground station.

22. The system of claim 21, wherein the at least one first collecting element comprises two or more downward-facing LEDs configured to collect radiation in a spectral band of< about 50 nm in a range of about 400 to about 1100 nm.

23. The system of claim 22, wherein the at least one second collecting element comprises two or more upward-facing LEDs configured to collect radiation in a spectral band of <50 nm in a range of about 400 to about 1100 nm.

24. The system of claim 19, wherein the remotely sensed imagery is collected by a satellite, an airplane, or a drone.

25. A method for determining agricultural conditions, the method comprising:
receiving, by an analysis server, remotely sensed imagery of an area in which a stationary ground station is installed, the remotely sensed imagery collected by a satellite, an airplane, or a drone and comprises radiance data;
receiving, by the analysis server, location coordinates from the stationary ground station, the location coordinates correspond to a fixed position of the stationary ground station;
receiving, by the analysis server, radiometric data from the stationary ground station, the radiometric data indicative of upwelling radiation and downwelling radiation measured by the stationary ground station;
generating, by the analysis server, color-corrected imagery as a function of the radiance data of the remotely sensed imagery and the radiometric data received from the stationary ground station; and
generating, by the analysis server, a mosaic image of the area based at least in part on the color-corrected imagery and the fixed position of the stationary ground station.

* * * * *